United States Patent [19]

Niizawa et al.

[11] Patent Number: 5,139,329

[45] Date of Patent: Aug. 18, 1992

[54] STANDARD SAMPLES AND METHODS OF INSTRUMENTAL MEASUREMENT OF SAYBOLT COLOR OF PETROLEUM PRODUCTS USING SAID SAMPLES

[75] Inventors: Akihiko Niizawa; Masahiro Yamaguchi, both of Yokohama, Japan

[73] Assignees: Nippon Petroleum Refining Co., Ltd.; The Japan Petroleum Institute, both of Tokyo, Japan

[21] Appl. No.: 748,553

[22] Filed: Aug. 22, 1991

[30] Foreign Application Priority Data

Aug. 30, 1990 [JP] Japan .................................. 2-227908

[51] Int. Cl.$^5$ ........................ G01N 33/22; G01N 33/26
[52] U.S. Cl. ......................................... 356/70; 356/243
[58] Field of Search ........................... 356/70, 243, 436

[56] References Cited

U.S. PATENT DOCUMENTS 3,951,854  4/1976  Sias et al. ........................ 356/70 X Primary Examiner—Vincent P. McGraw
Attorney, Agent, or Firm—Bucknam and Archer

[57] ABSTRACT

A standard sample for use in an instrumental measurement of Saybolt color of a petroleum product with a photoelectric colorimeter, which comprises a mixed solution of 1-(phenylazo)-2-naphthalenol, 3-methyl-1-phenyl-4-(phenylazo)-pyrazol-5-ol and 1,4-bis(-butylamino)-9,10-anthracenedione each as a colorant, 1-phenyl-1-xylylethane as a solvent for said colorants and dodecene as a diluent, and a method of instrumental measurement of Saybolt color of a petroleum product, which comprises calibrating a photoelectric colorimeter with the standard sample.

4 Claims, 1 Drawing Sheet

Color difference $\Delta E^*$ ab (CIE standard source C)

STANDARD SAMPLES AND METHODS OF INSTRUMENTAL MEASUREMENT OF SAYBOLT COLOR OF PETROLEUM PRODUCTS USING SAID SAMPLES

BACKGROUND OF THE INVENTION

1. Field of the Invention

The present invention relates to a standard sample used for instrumental measurement of Saybolt color with a photoelectric colorimeter (color and color difference meter) which is a color testing method for petroleum products such as kerosene and liquid paraffin, and a method of instrumental measurement of Saybolt color of a petroleum product using said sample.

2. Prior Art

There are two color testing methods for petroleum products, that is, the testing method for Saybolt color and the testing method for ASTM color which are prescribed in JIS K 2580.

Of these, the testing method for Saybolt color is applied to petroleum products having a high transparency, such as kerosene, liquid paraffin and paraffin wax, and symbolizes the brightness of a sample generally obtained by comparing the transmitted light through a standard colored glass with that through the sample by the use of a Saybolt chromometer. The color scale ranges from +30, the brightest, to −16, the darkest.

The Saybolt color as prescribed in JIS K 2580 is symbolized by the brightness of a sample obtained by comparing the transmitted light through a standard colored glass with that through the sample under test, and the standard colored glass is prescribed in its dispersion on the basis of the XYZ colorimetric method and the spectral transmittance by the use of the CIE standard illuminants C in accordance with JIS Z 8722.

However, since the judgement of the Saybolt color by the use of the Saybolt chromometer is visually conducted by a person in charge of measurement, the current situation is that a personal difference is apt to arise, thus bothering the person in the judgement. When the hue of a liquid is similar to that of a standard colored glass, the measured values agree with each other owing to small personal difference in brightness. However, when the hues of the above differ from each other, the personal difference increases.

Under such circumstances, automatization of such a testing method without resort to the visual measurement is eagerly desired at the present time.

In view of the above, an attempt was made by the present inventors to investigate whether or not a commercially available photoelectric colorimeter can be used for measuring the Saybolt color.

A measuring instrument used must be one in which a favorable correlation with the testing method as prescribed in JIS K 2580 is obtained in the entire range of the Saybolt color ranging from +30 to −16. Furthermore, a universal method of testing the color of material, especially that of liquid is desired.

As a method of measuring the color of material, the XYZ color system recommended by Commission Internationale de l'Eclairage (hereinafter abbreviated to "CIE") and prescribed in JIS Z 8722, and, as a method of specifying the color, the $L^*a^*b^*$ color system also recommended by CIE and prescribed in JIS Z 8729 are universal methods.

As a result of further investigation on the above-mentioned matter, it was decided by the present inventors to increase the optical path length of a commercially available measuring instrument (photoelectric colorimeter) from 20 mm to 100 mm to enhance the accuracy measurement. As a result, it was found that a favorable correlation existed between the Saybolt color (S: provisional name) and a color difference $\Delta E^*ab$ (E: provisional name) based on the $L^*a^*b^*$ color-specification method, as represented by the following calibration formula:

$$S = (\alpha/\log E - \beta) + \gamma$$

wherein $\alpha$, $\beta$ and $\gamma$ are each a constant.

As the above E value varies with an instrumental error depending on an instrument, it cannot be kept constant even for the same sample. It was necessary, therefore, to prepare a standard sample for Saybolt color to calibrate each instrument (photoelectric colorimeter) using the above sample.

Such a standard sample is required to be composed of a base material similar to a petroleum product, and have low volatility, low deterioration such as oxidation, with the elapse of time and good color stability.

There are available a method using a Hazen colorimetric standard solution prescribed in JIS K 2421 as the standard color solution, a method using platinum-cobalt scale prescribed in ASTM D-1209 and D-365 and the like. However, these methods are not suitable for measuring the Saybolt color, because a dark Saybolt color causes a different hue and each of the above solutions comprises an aqueous acid solution which corrodes a precision instrument to be used, thus making the operation troublesome.

SUMMARY OF THE INVENTION

It is an object of the present invention to provide a standard sample to be used for measuring Saybolt color by the use of a photoelectric colorimeter (color and color difference meter) and an instrumental measuring method using said sample on the basis of the above-mentioned viewpoint.

In attempts to achieve the above object, the present inventors made intensive studies and found that a colorant (dyestuff) having a hue coincident with the hue of a petroleum product, when dissolved in a specific solvent, coincides with a standard colored glass to be used in Saybolt colorimetry in regard to the hue and exhibits a sufficient availability as a standard sample.

The standard sample of the present invention comprises a mixed solution comprising 1-(phenylazo)-2-naphthalenol, 3-methyl-1-phenyl-4-(phenylazo)-pyrazol-5-ol and 1,4-bis(butylamino)-9,10-anthracenedione each as a colorant, 1-phenyl-1-xylylethane as a solvent for said colorants and dodecane as a diluent.

This invention will be explained hereunder in more detail.

Each of the colorants to be used in the present invention has the following chemical structure:

(1) 1-(phenylazo)-2-naphthalenol

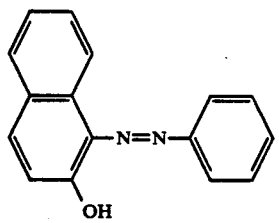

(CAS No. 842-07-9)
Color index (CI): Solvent yellow 14
Example: Oil Orange Extra (tradename)
(2) 3-methyl-1-phenyl-4-(phenylazo)-pyrazol-5-ol

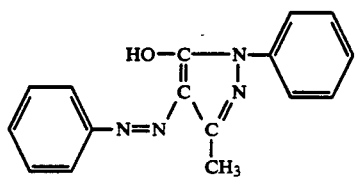

(CAS No. 4314-14-1)
Color index (CI): Solvent yellow 16
Example: Oil yellow 5GS Extra (tradename)
(3) 1,4-bis(butylamino)-9,10-anthracenedione

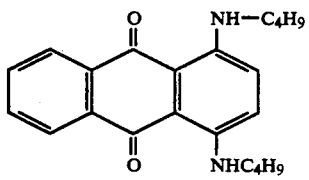

(CAS No. 17354-14-2)
Color index (CI): Solvent blue 35
Example: Oil Blue SB (tradename)

The above three colorants are most preferably mixed at a ratio by volume of (1):(2):(3) of 10:30:1.

In a standard sample of the present invention, 1-phenyl-1-xylylethane (hereinafter abbreviated to "PXE") and dodecane (hereinafter referred to as "n-$C_{12}$") are used as a solvent for the colorants and as a diluent, respectively.

With regard to the preparation of a specific standard sample, each of the colorants (dyestuffs) is mixed together at the above ratio to form 1,000 ppm (wt/vol %) of a dilute solution in PXE solvent, and the solution is diluted with n-$C_{12}$ prescribed times, for example, 250 to 20,000 times to be used as a standard sample.

In the following, the instrumental measuring method of the present invention will be described.

If the Saybolt color measured with the above-mentioned photoelectric colorimeter for a standard sample (having a true Saybolt color of +20) on the basis of the $\Delta E^*ab$ value of said sample and a predetermined calibration formula is 19.7, the Saybolt color thus measured is adjusted to 20 by the operation of the correction key at the operation-display section to calibrate the meter.

By carrying out the calibration (correction) of the meter with the standard samples each having a true Saybolt color of −15, 0, +15, +30 and so forth, in the same manner as above, the correct use of the meter is made possible.

As described hereinbefore, the instrumental measurement of the Saybolt color of a petroleum product can be carried out accurately without fail by the use of the standard sample of the present invention. Furthermore, the standard sample has a favorable color stability free from deterioration such as oxidation after the elapse of time.

DESCRIPTION OF THE PREFERRED EMBODIMENTS

Figure 1:
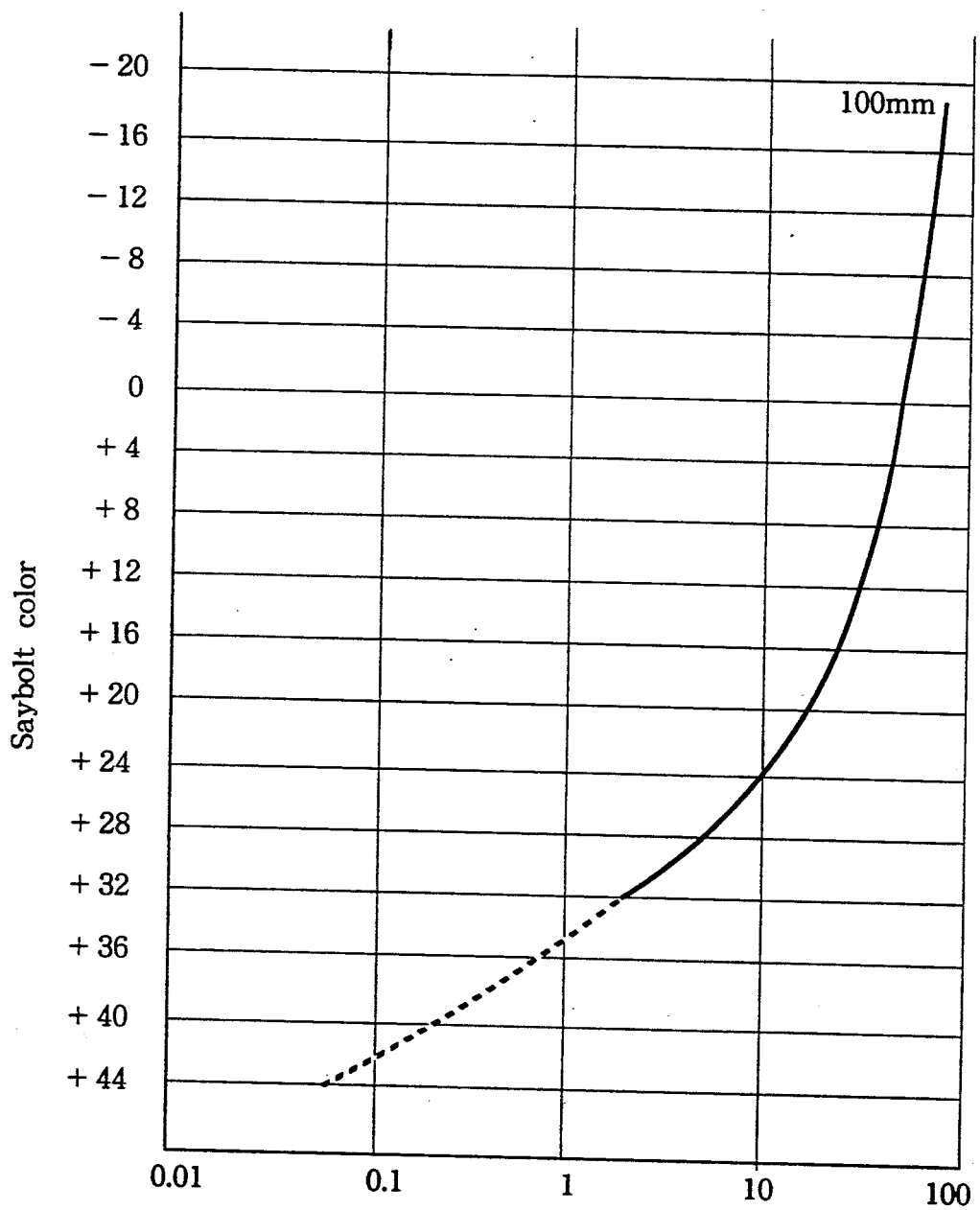
FIG. 1 is a graph showing the relation between $\Delta E^*ab$ and Saybolt color.

The present invention will be described in more detail by referring to the following Example.

EXAMPLE

Each of 17 standard samples having the Saybolt colors indicated in Table 1 was prepared by mixing 1-(phenylazo)-2-naphthalenol, 3-methyl-1-phenyl-4-(phenylazo)-pyrazol-5-ol and 1,4-bis(butylamino)-9,10-anthracenedione in a ratio by volume of 10:30:1, dissolving the obtained colorants mixture in 1-phenyl-1-xylylethane to obtain 1000 ppm (wt/vol %) of PXE solution, and then diluting the obtained solution with n-$C_{12}$ with a dilution as specified in Table 1. $\Delta E^*ab$ value of each of said samples was measured by the use of a photoelectric colorimeter (chroma meter CT-210 custom, produced by Minolta Camera Co., Ltd.) in which a sampling cell having a length of 100 mm and a CIE standard source C were employed. The results are shown in Table 1 and FIG. 1.

TABLE 1

| Standard sample No. | Dilution | Saybolt color | $\Delta E^*ab$ |
| --- | --- | --- | --- |
| 1 | 250 | (−18) | 81.19 |
| 2 | 275 | −16 | 76.73 |
| 3 | 285 | −15 | 75.28 |
| 4 | 350 | −10 | 65.70 |
| 5 | 400 | −8 | 62.10 |
| 6 | 500 | −2 | 51.30 |
| 7 | 550 | 0 | 47.78 |
| 8 | 1000 | +10 | 29.58 |
| 9 | 1450 | +15 | 21.49 |
| 10 | 2000 | +18 | 16.40 |
| 11 | 2600 | +20 | 13.24 |
| 12 | 3200 | +21 | 11.32 |
| 13 | 4000 | +23 | 8.82 |
| 14 | 5300 | +25 | 7.27 |
| 15 | 10000 | +28 | 4.31 |
| 16 | 12500 | +30 | 2.65 |
| 17 | 20000 | +32 | 1.58 |

As is apparent from Table 1 and FIG. 1, $\Delta E^*ab$ value of each of the standard samples corresponds appropriately to each Saybolt color. Furthermore, with respect to the reproducibility of $\Delta E^*ab$ value, the reproduction error was as small as 0.15 or less. Still furthermore, the standard samples were almost free from any change in $\Delta E^*ab$ value even after a storage in a dark place for 4 months, thus demonstrating their excellent storage stability.

What is claimed is:

1. A standard sample for use in an instrumental measurement of Saybolt color of a petroleum product with a photoelectric colorimeter, which comprises a mixed solution of 1-(phenylazo)-2-naphthalenol, 3-methyl-1-phenyl-4-(phenylazo)-pyrazol-5-ol and 1,4-bis(-butylamino)-9,10-anthracenedione each as a colorant, 1-phenyl-1-xylylethane as a solvent for said colorants and dodecane as a diluent.

2. The standard sample according to claim 1, wherein said colorants 1-(phenylazo)-2-naphthalenol, 3-methyl-1-phenyl-4-(phenylazo)-pyrazol-5-ol and 1,4-bis(butylamino)-9,10-anthracenedione are compounded at a ratio by volume of 10:30:1.

3. A method of instrumental measurement of Saybolt color of a petroleum product with a photoelectric colorimeter, which comprises calibrating the photoelectric colorimeter by the use of the standard sample comprising a mixed solution of 1-(phenylazo)-2-naphthalenol, 3-methyl-1-phenyl-4-(phenylazo)-pyrazol-5-ol and 1,4-bis(butylamino)-9,10-anthracenedione each as a colorant, 1-phenyl-1-xylylethane as a solvent for said colorants and dodecane as a diluent.

4. The method according to claim 3, wherein said colorants 1-(phenylazo)-2-naphthalenol, 3-methyl-1-phenyl-4-(phenylazo)-pyrazol-5-ol and 1,4-bis(butylamino)-9,10-anthracenedione are compounded at a ratio by volume of 10:30:1.

* * * * *